(12) United States Patent
Arnott

(10) Patent No.: US 7,056,328 B2
(45) Date of Patent: Jun. 6, 2006

(54) APPARATUS FOR CAPTURING OBJECTS BEYOND AN OPERATIVE SITE UTILIZING A CAPTURE DEVICE DELIVERED ON A MEDICAL GUIDE WIRE

(76) Inventor: Richard J. Arnott, 113 Hodil Ter., Pittsburgh, PA (US) 15238

( * ) Notice: Subject to any disclaimer, the term of this patent is extended or adjusted under 35 U.S.C. 154(b) by 66 days.

(21) Appl. No.: 10/246,001

(22) Filed: Sep. 18, 2002

(65) Prior Publication Data

US 2004/0087971 A1    May 6, 2004

(51) Int. Cl.
*A61M 29/00* (2006.01)
(52) U.S. Cl. ........................................ 606/200; 606/113
(58) Field of Classification Search ................ 606/200, 606/113, 114; 600/585
See application file for complete search history.

(56) References Cited

U.S. PATENT DOCUMENTS

| | | | | |
|---|---|---|---|---|
| 5,910,154 A | * | 6/1999 | Tsugita et al. ............... | 606/200 |
| 6,042,598 A | * | 3/2000 | Tsugita et al. ............... | 606/200 |
| 6,152,946 A | * | 11/2000 | Broome et al. ............... | 606/200 |
| 6,245,012 B1 | | 6/2001 | Kleshinski | |
| 6,277,138 B1 | | 8/2001 | Levinson et al. | |
| 6,361,546 B1 | | 3/2002 | Khosravi | |
| 6,432,122 B1 | | 8/2002 | Gilson et al. | |
| 6,616,682 B1 | * | 9/2003 | Joergensen et al. ......... | 606/200 |
| 6,652,554 B1 | * | 11/2003 | Wholey et al. ............... | 606/200 |
| 6,974,469 B1 | * | 12/2005 | Broome et al. ............... | 606/200 |
| 2002/0055747 A1 | | 5/2002 | Cano et al. | |
| 2002/0123720 A1 | * | 9/2002 | Kusleika et al. ............. | 604/108 |

* cited by examiner

*Primary Examiner*—Julian W. Woo
(74) *Attorney, Agent, or Firm*—McKay & Associates, P.C.

(57) ABSTRACT

An apparatus for removing a solid object from a body canal or vessel includes a coil of wire configured to slidably receive a guide wire and a sack having a mouth and a closed bottom opposite the sack. A resilient frame is connected between the coil of wire and the sack for biasing the mouth of the sack open around the coil of wire. The resilient frame is positionable between a collapsed state where the mouth of the sack is closed against the bias of the resilient frame and a deployed state where the mouth of the sack is biased open by the resilient frame.

4 Claims, 9 Drawing Sheets

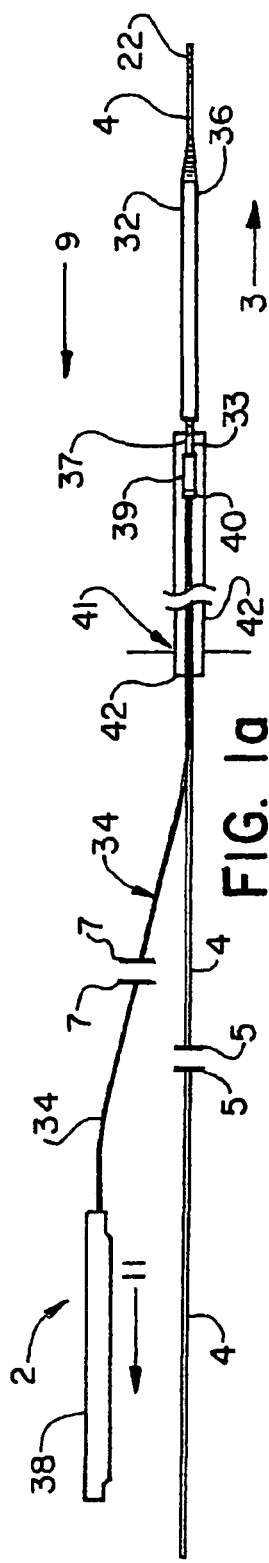
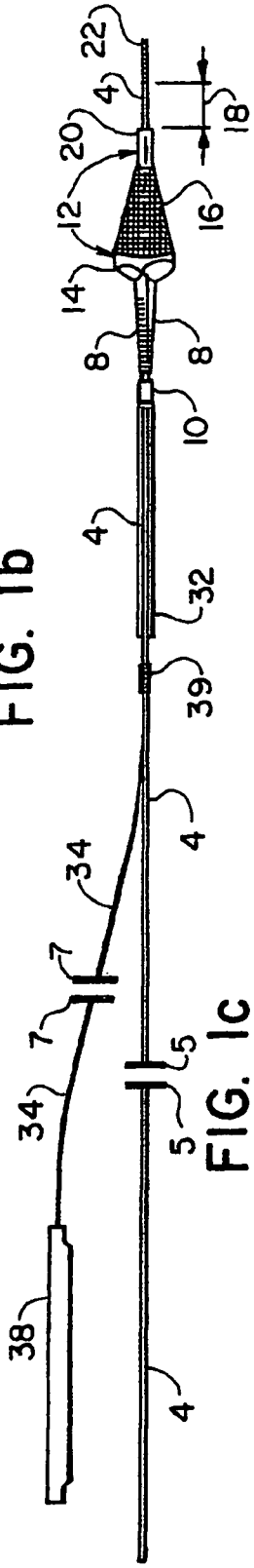
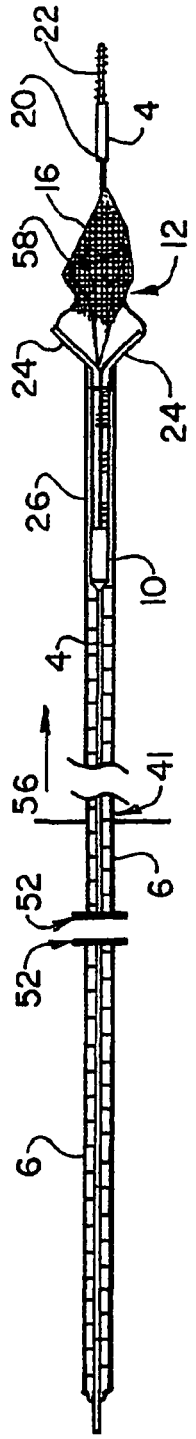

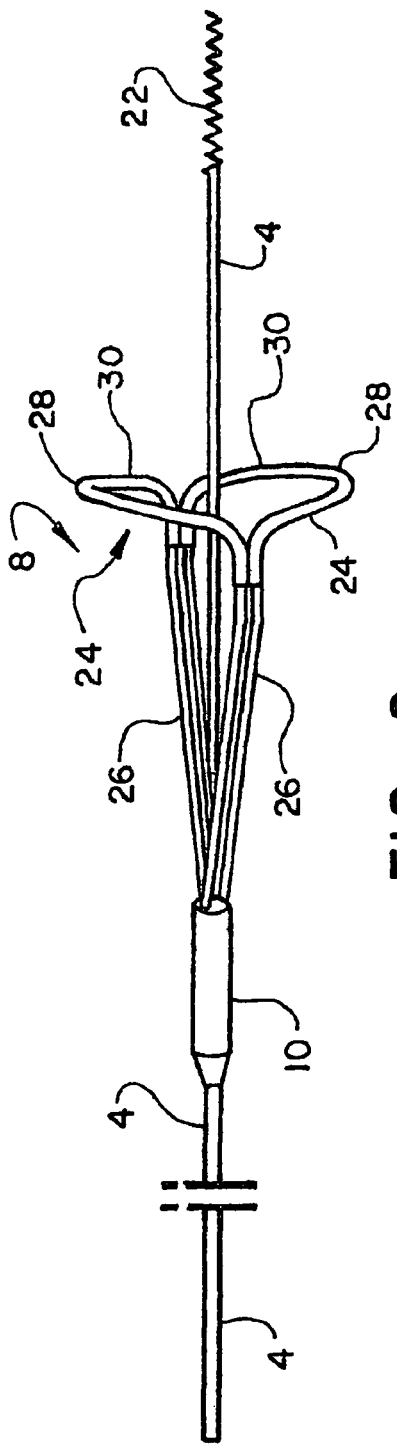
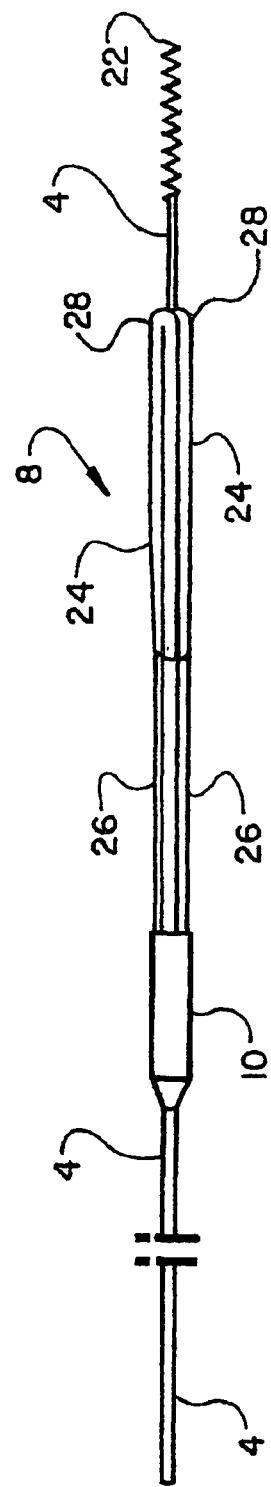
FIG. 2
FIG. 3

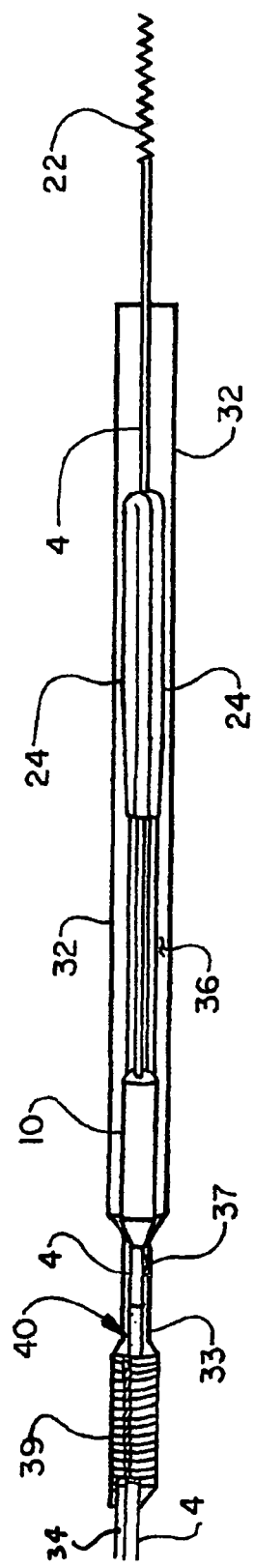
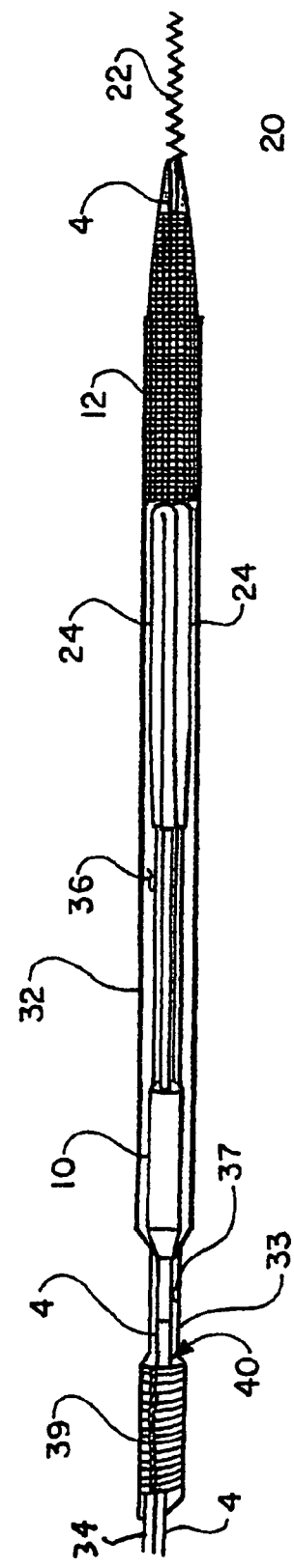
FIG. 4
FIG. 5

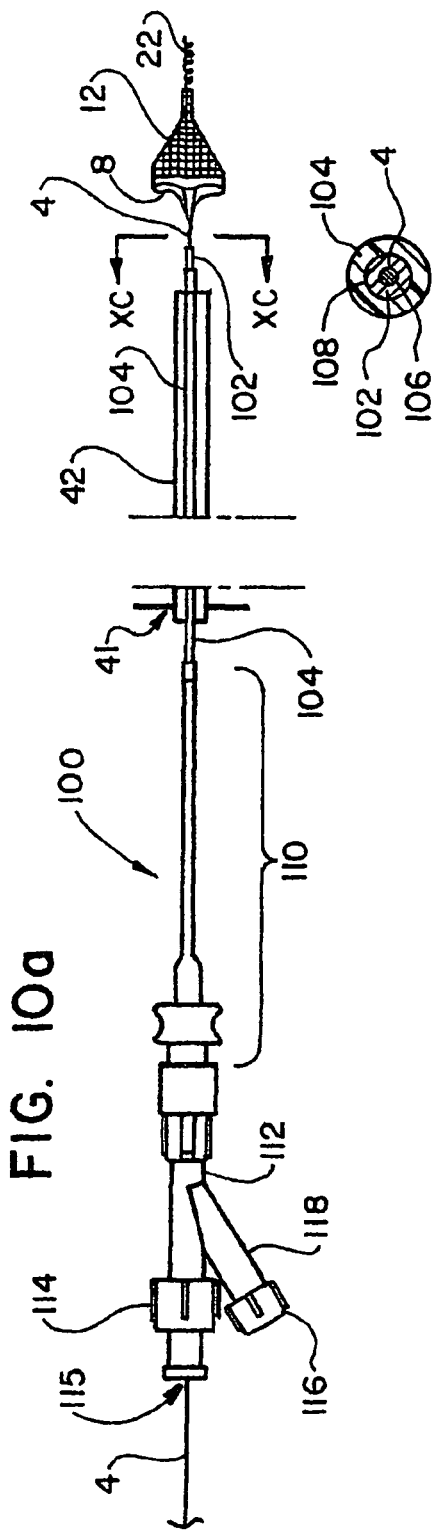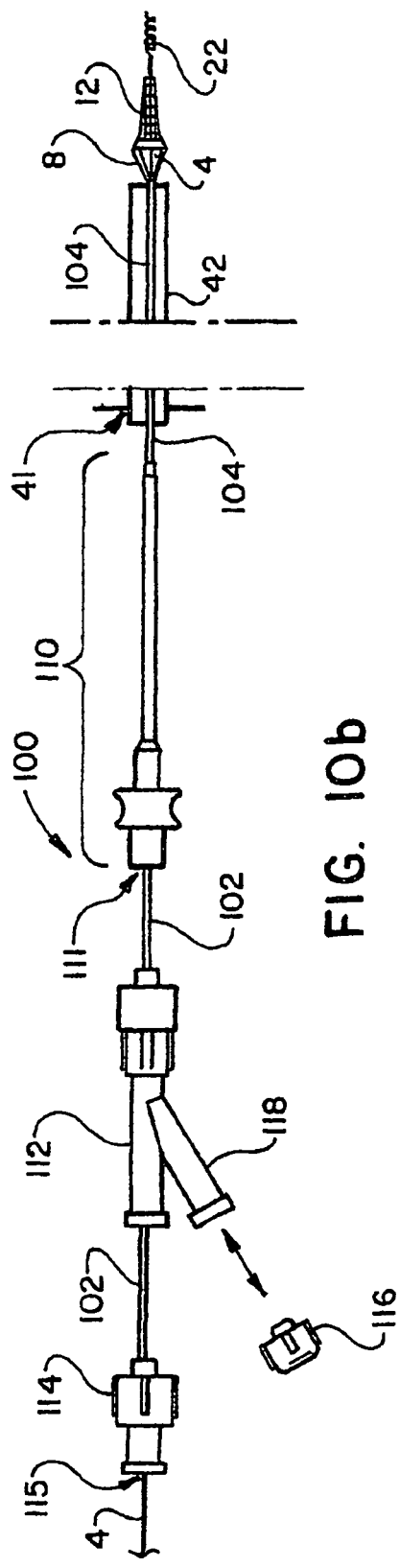

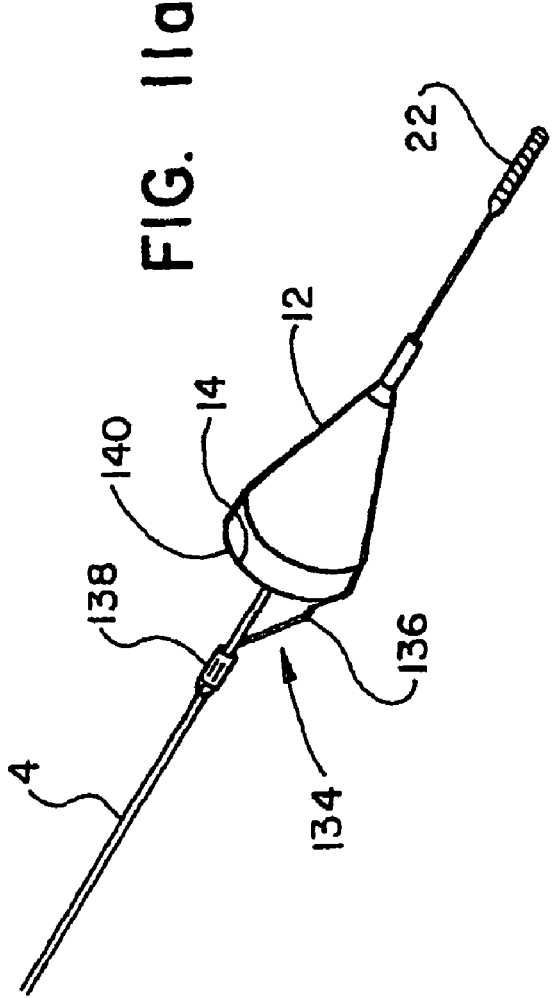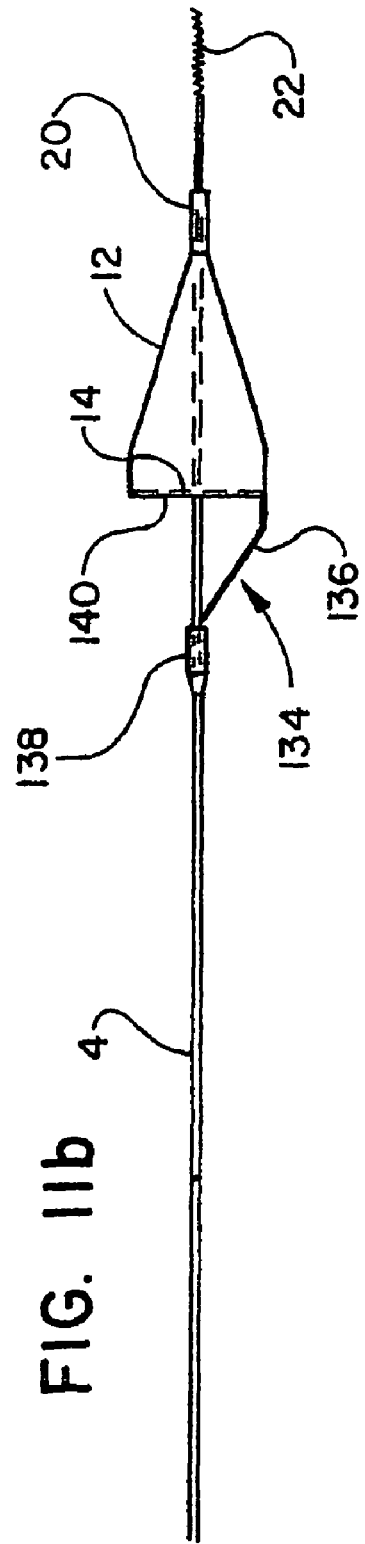

APPARATUS FOR CAPTURING OBJECTS BEYOND AN OPERATIVE SITE UTILIZING A CAPTURE DEVICE DELIVERED ON A MEDICAL GUIDE WIRE

BACKGROUND

1. Field of the Invention

The present invention is directed to capturing objects beyond an operative site in any of a variety of medical procedures employed to treat any number of medical conditions in human and/or animal patients.

2. Description of the Prior Art

In many medical procedures, objects are dislodged or otherwise freed by the surgeon during the surgical procedure, and it is useful and/or necessary to capture the dislodged and/or otherwise freed object.

Although minimally invasive interventional medical therapies in general, and minimally invasive endovascular therapy in particular, are medical procedures where objects may be dislodged or otherwise freed during the procedure, each has enjoyed unprecedented expansion to treat patients because of the numerous medical benefits associated with not having to enter the body through more invasive surgical techniques. These benefits include, but are not limited to, less trauma and/or scarring for patients, less time to heal, less risk of infection and decreased hospital stays, to name but a few.

More particularly, minimally invasive endovascular therapy is often used to treat diseased vessels, e.g., arteries and veins. With such therapy, small instruments are inserted into the vessels through a puncture or access opening made in one of the vessels at an entry site and are advanced through the circulatory system to an operative site where the vessel has become diseased, and the instruments are used to repair the diseased or operative site.

Typically, the goal of such therapy is to dilate full or partial blockages of the diseased vessel. Such blockages may have developed over time or may have developed quickly, as for example, in response to an injury. One common source of such blockage is thromboemboli which has formed in the vessel. Thrombus is an aggregation of platelets, fibrin, clotting factors and cellular components of blood that spontaneously form and attach on the interior wall of a vein or artery, and thromboemboli are emboli of thrombus which operate to partially or completely occlude the interior or lumen of the blood or other vessel.

Techniques to open and/or maintain the dilation of the partially or completely occluded lumen of blood or other vessels include positioning a balloon across an obstruction or partially occluded section of the vessel, inflating the balloon to compress the build up (balloon angioplasty) and/or temporarily or permanently inserting a tube-like support within the vessels to keep the vessel open (stenting).

Minimally invasive endovascular therapy has the significant advantage that it is less invasive than traditional surgical techniques and causes less trauma to the patient. However, this therapy is complicated by the fact that it can undesirably dislodge or free particles/objects during the procedure as discussed above, and in that the tools or instruments and workspace, e.g., the interior of the vessels of the body, are in some cases extremely small and close, and reaching the operative site with the tools is very difficult in some instances due to the considerable branching of the circulatory system that may occur between the entry site into the blood vessel and the operative site. This therapy is further complicated by the fact that the entry site is often far from the operative site, as for example, where the entry site is in the thigh at the femoral artery and the operative site is located in the neck at the carotid artery. Even when the surgeon's instruments have been properly advanced to the operative site, manipulating the tools to perform their respective functions at the operative site is often difficult for the surgeon due to many factors including the close quarters at the operative site and the distance between the entry site and the operative site.

One method and apparatus commonly used by surgeons to ensure the tools reach the operative site is to first thread a simple guide wire to or beyond the operative site. Thereafter, various tools are threaded over the guide wire by the surgeon to reach the operative site. It is an important aspect of such guide wires that they must be easy to manipulate through the vessels, including in certain cases, through lesions or areas of blockage in the vessel by the surgeon. In addition to exhibiting sufficient resiliency so as to be pushable in the vessel, the guide wire must exhibit sufficient flexibility and maneuverability to enable the surgeon to traverse the many twists and turns of the circulatory (or other) system to reach the operative site.

An aspect of the ability for a surgeon to manipulate the guide wire through the circulatory or other system is the guide wire's "torquability". As defined herein, the term "torquability" means that as the surgeon rotates the proximal region of the guide wire that extends outside of the patient's body during the advancement of the guide wire through the patient's blood or other vessels to the operative site, the amount of rotation at the proximal region of the guide wire is transmitted to the distal end of the guide wire being inserted and advanced through the patient's blood or other vessels to the operative site. A lack of correlation between rotation at the proximal region of the guide wire and rotation at the distal end of the guide wire is referred to as reduced torquability and is undesirable. A high degree of correlation is referred to as a high degree of torquability and is desirable. As may be appreciated, it is most desirable for the guide wire to have an exact correlation or high torquability between the rotation applied proximally at the proximal region of the guide wire and the rotation developed distally in the guide wire, so that the surgeon can carefully control and direct the medical guide wire. With known devices, there is considerable difference between the amount of rotation applied at the proximal region of the guide wire and the amount of rotation developed at the distal end of the guide wire, making it very difficult for surgeons to maneuver the distal end of the guide wire.

Even where the guide wire exhibits the desired torquability characteristics, and the tools have been properly threaded to the operative site and have been properly manipulated to perform their respective functions at the operative site, there remains the problem noted above, namely, that the process of dilating the occlusion and/or inserting the stent may dislodge or free small particles or objects, also known, among other things, as clots, fragments, plaque, emboli, thromboemboli, etc. More particularly, with respect to endovascular therapy, the term "embolic event" has come to be used to describe complications where thrombus or plaque is shed inadvertently from a lesion to migrate to smaller vessels beyond the operative site to create a full or partial occlusion of the lumen of the vessel or vessels. This is most undesirable and can lead to many complications. Complications depend upon the site in the body where such emboli lodge downstream of the operative site, but may include stroke, myocardial infarction, kidney failure, limb loss or even death. With increasing vigor, surgeons have expressed the need to reduce the likelihood of such complications so that protection against embolic events will become a standard component of endovascular therapy.

Devices have been made in the art to capture objects, including emboli, downstream of an operative site in medical procedures, including endovascular therapy. Such devices generally employ a capture device, such as a bag or filter, which has a collapsed state and an expanded or deployed state. Typically, the capture device is maintained in its collapsed state within sheathing and is inserted into the blood or other vessel and is threaded beyond the operative site. It is then ejected from the sheathing whereupon it expands to its deployed state to capture the objects dislodged or otherwise freed during the medical procedure.

One device for removing clot or filtering particles from blood is described in U.S. Pat. No. 4,723,549 to Wholey et al., which discloses a device for dilating occluded blood vessels. This device includes a collapsible filter device positioned between a dilating balloon and the distal end of the catheter. The filter comprises a plurality of resilient ribs secured to the catheter that extend axially toward the dilating balloon. Filter material is secured to the ribs. The filter deploys as a balloon is inflated to form a cup-shaped trap. An important limitation of the Wholey et al. device appears to be that the filter does not seal around the interior vessel wall. Thus, particles sought to be trapped in the filter can instead undesirably pass between the filter and the vessel wall and flow downstream in the circulatory system to produce a blockage. Another limitation is that the device also presents a large profile during positioning. Yet another limitation appears to be that the device is difficult to construct.

U.S. Pat. No. 4,873,978 to Ginsburg discloses a vascular catheter that includes a strainer device at its distal end. The device is inserted into a vessel downstream from the treatment site and advanced to a proximal downstream location. The filter is contained in a sheath when closed. When pushed from the sheath, the filter deploys such that its mouth spans the lumen of the vessel. Deployment is by expansion of resilient tines to which the strainer material is attached. Again, however, it appears that the filter does not seal around the interior vessel wall, thus undesirably allowing particles to bypass the filter by passing between the filter and the vessel wall. The position of the mouth relative to the sheath is also clinically limiting for the Ginsburg device.

U.S. Pat. No. 5,695,519 to Summers et al. discloses a removable intravascular filter on a hollow guide wire for entrapping and retaining emboli. The filter is deployable by manipulation of an actuating wire that extends from the filter into and through the hollow tube and out the proximal end. One limitation with the Summers et al. device appears to be that its filter material is not fully constrained. Therefore, during positioning within a vessel, as the device is positioned through and past a clot, the filter material can snag clot material undesirably creating freely floating emboli. It is unclear if the actuating wire can close the filter, and it appears in any event that it will exert a pull force on the rim of the filter that could tear the wire from the rim. Another limitation appears to be that the device application is limited by the diameter of the tube needed to contain the actuating wire.

U.S. Pat. No. 5,814,064 to Daniel et al. discloses an emboli capture device on a guide wire. The filter material is coupled to a distal portion of the guide wire and is expanded across the lumen of a vessel by a fluid activated expandable member in communication with a lumen running the length of the guide wire. One limitation of the device appears to be that during positioning, as the device is passed through and beyond the clot, filter material may interact with the clot so as to undesirably dislodge material and produce emboli. It is further believed that the device may also be difficult to manufacture. Another limitation is that it is difficult to determine the amount of fluid needed to expand the member. A lack of control can rupture and tear the smaller vessels. Thus, the Daniel et al. device would appear to be more compatible with use in the larger vessels only.

PCT Publication No. WO 98/33443 discloses a removable vascular filter wherein the filter material is fixed to cables or spines mounted to a central guide wire. A movable core or fibers inside the guide wire can be utilized to transition the cables or spines from approximately parallel the guide wire to approximately perpendicular the guide wire. A limitation of this device appears to be that the filter does not seal around the interior vessel wall. Thus, particles, e.g., emboli-forming materials, can undesirably bypass the filter by passing between the filter and the vessel wall. Another limitation appears to be that this umbrella-type device is shallow when deployed so that, as it is being closed for removal, the particles it was able to ensnare could escape. Yet another limitation is that the frame is such that the introduction profile presents a risk of generating emboli as the device is passed through and beyond the clot, occlusion or stenosis.

U.S. Pat. No. 5,769,816 to Barbut et al. discloses a device for filtering blood within a blood vessel. The device is delivered through a cannula and consists generally of a cone-shaped mesh with apex attached to a central support and open edge attached to an inflation seal that can be deflated or inflated. The seal is deflated during delivery and when delivery is complete, it is inflated to seal the filter around the lumen of the vessel. Limitations of this device include that it is complex to manufacture. Inflation and deflation of the seal adds additional operative steps thus prolonging the operation-and introducing the issue again of control, e.g., of how much to inflate to obtain a seal without causing damage to the vessel or other material. While the device may be suitable for large vessels, such as the aorta, is would be most difficult to scale for smaller vessels, such as the carotid or the coronary arteries.

U.S. Pat. No. 5,549,626 to Miller et al. discloses a coaxial filter device for removing particles from arteries and veins consisting of an outer catheter that can be inserted into a blood vessel and an inner catheter with a filter at its distal end. The filter is a radially expandable receptacle made of an elastic mesh structure of spring wires or plastic monofilaments. When pushed from the distal end of the catheter, the filter deploys across the vessel lumen. A syringe attached to the proximal end of the inner catheter aspirates particles entrapped in the filter. One limitation of this device appears to be that it is possible that some particles will remain in the filter after aspiration such that, when the filter is retracted into the outer catheter, particles not aspirated are undesirably released into the circulatory system.

U.S. Pat. No. 6,027,520 to Tsugita et al. discloses a method and system for embolic protection consisting of a filter on a guide wire coupled with a separate stent catheter deployed over the guide wire. One limitation of the Tsugita et al. device is that the many filter designs summarized in the patent generally lack a controllable, conformable circumferential support in the mouth of the filters to ensure they seal around the inside of a blood vessel. Without such a seal, it is again possible for particulate material to evade the filter by undesirably passing between the filter and the vessel wall, whereupon the particulate material may flow downstream of the operative or other site to produce full or partial blockage of the vessels. Many of the Tsugita et al. filter expansion devices utilize multiple struts to open the filter. These are not desirable as they increase the profile of the device when crossing a lesion, in turn, reducing the range of clinical cases on which they can be used. Further, such designs add stiffness to the region of the undeployed filter which can impede the surgeon's ability to direct the guide wire through the complex twists and turns of the circulatory system to the operative site, e.g., making it difficult to direct the device into a branching vessel. Also, the Tsugita et al. design is burdened by its use of a long deployment sheath to hold the filter in a collapsed state and direct it to the operative site. The Tsugita et al. sheath extends from a hemostatic seal at the site of entry into the blood or other vessel to the operative site (see column 7, lines 56–58. and also column 8, lines 19–30 of the Tsugita et al. patent). This long sheath, necessary in the Tsugita et al. design, significantly impairs the ability to direct the guide wire through the circulatory system to the operative site. Not only is such a sheath an impairment to directing the guide wire around the twists and turns of the circulatory system, but such a sheath also "loads" the guide wire, which operates to significantly reduce the Tsugita et al. system's torquability, greatly reducing the ability of the surgeon to control the guide wire and guide it through tight lesions.

At column 7, lines 28–32, Tsugita et al. states that its stent may comprise a tube, sheet, wire, mesh or spring, and goes on to state that such a stent can cover the plaque and substantially permanently trap it between the stent and the wall of the vessel. (see column 9, lines 55–58 of the Tsugita et al. patent) However, this is not accurate, and depending upon the type of stent, not only will it not trap such plaque, but plaque can reform through the interstices of the mesh whereupon the vessel can again become fully or partially occluded.

These shortcomings are present whether the stent is mechanically expandable or self expanding. Relative to mechanically expandable stents, they are delivered with a stent catheter. See U.S. Pat. Nos. 5,507,768; 5,158,548 and 5,242,399 to Lau et al. incorporated herein by reference. The catheter has an inflatable balloon at or near the distal end on which the stent is mounted. An inflation lumen runs the length of the catheter to the balloon. Generally, the stent is a tubular mesh sleeve. See U.S. Pat. No. 4,733,665 to Palmaz incorporated herein by reference. A self-expanding stent is typically made of Nitinol. It is compressed within a catheter until deployment. It is pushed from the catheter to deploy it. Both types of stents tend to create embolic particles. Also, both allow stenotic material to build up through the interstices of the wire mesh that could again occlude the artery.

Permanent filters for the vena cava are well-established clinical devices. These open filters capture large emboli passing from a surgical site to the lungs. U.S. Pat. No. 3,952,747 to Kimmell, Jr. et al. discloses the Kimray-Greenfield filter. It is a permanent filter typically placed in the vena cava and consists of a plurality of convergent legs in a generally conical array Each leg has a hook at its end to impale the interior wall of the vena cava. U.S. Pat. Nos. that are joined at their convergent ends to an apical hub. U.S. Pat. No. 4,425,908 to Simon; U.S. Pat. No. 4,688,553 to Metals; and U.S. Pat. No. 4,727,873 to Mobin-Uddin are also illustrative of such devices.

U.S. Pat. Nos. 5,669,933 and 5,836,968 to Simon et al. are illustrative of removable blood clot filters suitable for the venous system, specifically the vena cava.

However, the presently available capture devices all suffer from the limitation that they are not easily manipulated in the patient's body. They usually include tube-like sheathing material which extends all along the length of the guide wire used to insert the capture device into the vessel, generally extending from the entry site into the body, also known as an access port or access opening to the operative site, which sheathing operates to contain the capture device until its desired deployment in the vessel beyond the operative site. Such sheathing material operates to reduce torquability of the guide wire used to insert the capture device and operates to significantly reduce the flexibility of wire within the circulatory or other system as noted above. Removal without causing excessive movement of the deployed filter is also a problem. As the sheath is pulled from the access port during removal, the surgeon must continually reposition his hand to hold the wire used to insert the capture device, that is, as the sheath is pulled through the access port, the surgeon must release the wire and then re-grasp further down from the access port. As the surgeon's hand grasps the wire further from the access port, the more difficult it becomes to steady the guide wire as the sheath is withdrawn. As such, the capture device may move back and forth, and as it is generally at this point in its expanded state, the constant rubbing of the wall of the blood or other vessel or canal by the capturing device may irritate or injure the wall of the blood or other vessel or canal. Another complication is that several capture devices include bulky or complex deployment mechanisms, and further, when deployed, fail to fully seal around the interior of the vessel or other wall or fail to prevent unwanted release of captured particles, fragments, objects, emboli, etc., whereupon such particles, fragments, objects, emboli, etc. can undesirably escape and travel beyond the capture device.

Thus, there is a need in the art for a capture device and methods of constructing and using such device, which is easily threaded through the vessels or canals of humans and/or animals to reach an operative site, which exhibits excellent torquability, flexibility and maneuverability, which is easily removable along with its captured objects once the medical procedure has been completed without injuring or irritating the wall of the vessel or canal, and which forms a seal with the wall of the vessel or canal or otherwise prevents the undesirable escape of particles, fragments, objects, emboli, etc. beyond the capture device during surgery. There also is a need in the art for a system of associating surgical tools with such a capture device to provide protection downstream of an operative site for the capture of objects dislodged and/or freed during the medical procedure.

SUMMARY OF THE INVENTION

Accordingly, I have invented an apparatus for removing a solid object from a body canal or vessel. The apparatus includes a coil of wire configured to slidably receive a guide wire and a sack having a mouth and a closed bottom opposite the mouth. A resilient frame is connected between the coil of wire and the sack for biasing the mouth of the sack opened around the coil of wire. The resilient frame is positionable between a collapsed state where the mouth of the sack is closed against the bias of the resilient frame and a deployed state where the mouth of the sack is biased open by the resilient frame.

The apparatus can include a containment collar configured to slidably receive the guide wire therethrough and to receive the resilient frame therein. A pull wire can be connected to the containment collar so that in response to relative movement between the guide wire and the pull wire, the resilient frame is positionable between the collapsed state inside the containment collar and the deployed state outside the containment collar. The guide wire can include a proximal stop and a distal stop in spaced relation on the guide wire. The coil of wire can be received on the guide wire between the proximal stop and the distal stop and each stop can be configured to avoid the slidable passage of the coil of wire thereby.

Preferably, the closed bottom of the sack is connected to the coil of wire adjacent one end thereof, the resilient frame is connected to the coil of wire adjacent the end thereof opposite the closed bottom of the sack, and the mouth of the sack is connected to the wire frame between the ends of the coil of wire.

The apparatus can include a deployment catheter having a lumen configured to slidably receive the guide wire. The guide wire can include a distal stop configured to avoid the slidable passage of the coil of wire thereby. The deployment catheter can have an end configured to abut an end of the coil of wire when the coil of wire is received on the guide wire between the deployment catheter and the distal stop.

Alternatively, the apparatus can include a deployment catheter having a lumen configured to slidably receive the guide wire and at least part of the resilient frame therein so that in response to relative movement between the guide wire and the deployment catheter, the resilient frame is positionable between the collapsed state at least partially inside the deployment catheter and the deployed state outside the deployment catheter.

Preferably the coil of wire is a helically wound spring that is firm axially and pliable laterally.

BRIEF DESCRIPTION OF THE DRAWINGS

FIGS. 1A–1D are side views of a device for capturing objects beyond an operative site utilizing a capture device in accordance with the present invention mounted on a guide wire.

FIG. 2 is a perspective view of a wire frame of the capture device of FIGS. 1A–1D, with the wire frame in its deployed state.

FIG. 3 is a side view of the wire frame in FIG. 2 in its collapsed state.

FIG. 4 is a side view of the collapsed wire frame shown in FIG. 3 received within a containment collar in accordance with the present invention.

FIG. 5 is a side view of the collapsed wire frame and containment collar of FIG. 4 with a filter or sack connected to the wire frame and retracted partially into the containment collar.

FIG. 10A is a side view of a retrieval catheter assembly received on a guide wire in its undeployed state.

FIG. 10B is a side view of the retrieval catheter assembly shown in FIG. 10A in a partially deployed state where a wire frame attached to the guide wire is partially retracted into a sheath of the retrieval catheter assembly.

FIG. 10C is a section taken along lines XC—XC in FIG. 10A.

FIGS. 11A and 11B are perspective and side views, respectively, of another embodiment of a capture device of the present invention.

DETAILED DESCRIPTION OF THE PREFERRED EMBODIMENTS

Figure 6:
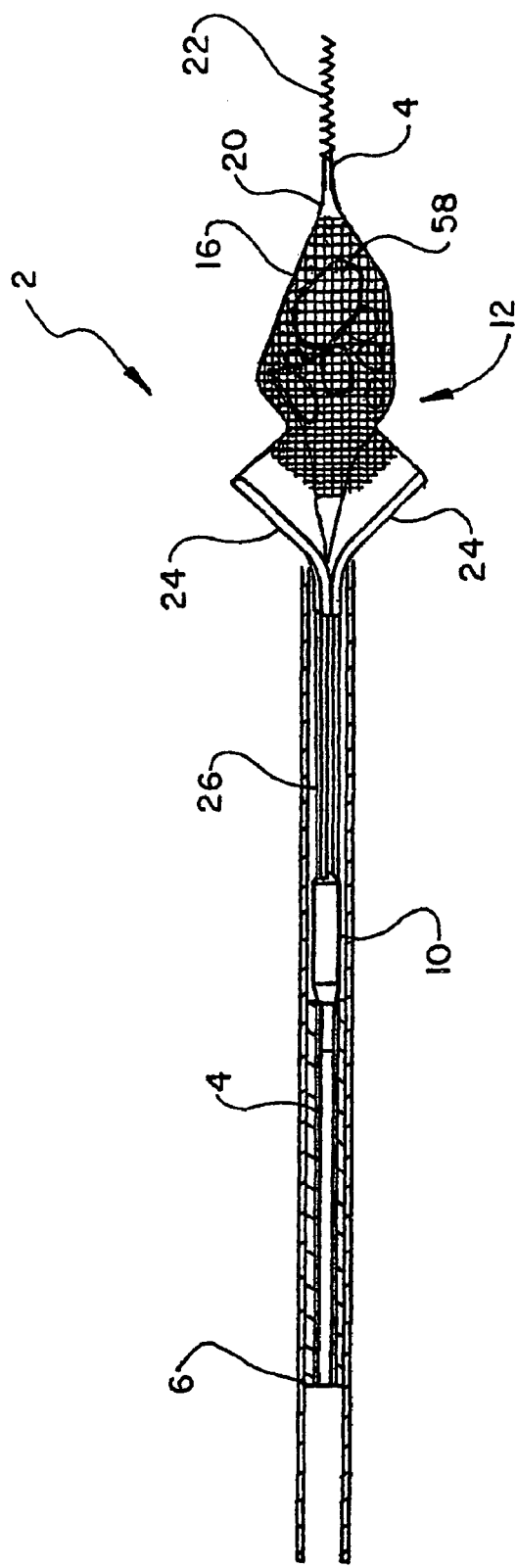
FIG. 6 is a partial cross-sectional side view of a partially deployed wire frame and filter of FIG. 5 with particles captured in the filter.

The present invention relates generally to a method and apparatus for capturing objects beyond an operative site in any of a variety of medical procedures employed to treat any number of medical conditions in human and/or animal patients.

More particularly, the apparatus of the present invention includes in one embodiment, a novel object capture device integrally incorporated as part of a medical guide wire or otherwise mounted on or affixed to a medical guide wire, which medical guide wire is inserted into the human or animal patient and is threaded or otherwise advanced in the body through one or more of the body's canals or vessels to and/or beyond an operative site. As disclosed in more detail below, the novel object capture device includes a frame having a sack or filter attached thereto, and the object capture device operates to capture objects, e.g., emboli, beyond the operative site.

The present invention includes in yet another embodiment, a system for the endovascular treatment of blood or other vessels which includes the combination of the capture device on a medical guide wire with other devices, e.g., endovascular devices, such as dilation balloon systems, stent deployment systems, mechanical and/or laser thrombectomy devices and combinations thereof, that track over the guide wire, for use in medical procedures to treat humans and/or animals.

The methods of the present invention include methods of constructing the apparatus and system of the present invention, and methods of using the novel object capture device of the present invention to treat medical conditions in human and/or animal patients.

Referring now to FIGS. 1A–1D, an "on-the-wire" endovascular device 2 for capturing and removing objects, particles and/or other solid or semi-solid matter in blood or other vessels, organs, canals and/or body cavities of a patient according to the teachings of the present invention is shown. The following description of endovascular device 2 will also illustrate one or more embodiments of a method for insertion and removal of the device in a blood or other vessel in the body.

FIGS. 1A and 1B illustrate endovascular device 2 in its collapsed state or structure where an object capturing filter which includes a resilient frame, preferably a resilient wire frame 8, and a sack 12 affixed to wire frame 8, described in more detail below, is contained within a containment collar 32.

More particularly, starting at the right side of endovascular device 2 as viewed from the orientation of an observer viewing FIG. 1A, endovascular device 2 includes an elongated guide wire 4 received in and through containment collar 32. The length of guide wire 4 is not limiting to the present invention, and may be of any length necessary to extend from an entry site or access opening 41 into a body canal or vessel to the operative site. Break lines 5 shown in FIG. 1A illustrate that the length of endovascular device 2 may be modified as necessary for a given surgical application.

As shown in FIG. 1A, containment collar 32 can be constructed of an opaque material. However, as shown in FIGS. 1B–1D, containment collar 32 can also be constructed of a transparent material. Suitable materials for the construction of containment collar 32 are described below.

A pliable tip 22 is preferably connected to or integrally formed as part of the distal end of guide wire 4. Pliable tip 22 is preferably formed from a biocompatible material having a spring memory. Suitable materials for the construction of pliable tip 22 include platinum wire. Preferably, the biocompatible material forming pliable tip 22 is wound into a coil with one end of pliable tip 22 attached to the distal end of guide wire 4 and with the other end of pliable tip 22 extending away from guide wire 4. Pliable tip 22 facilitates the advancement of the distal end of guide wire 4 and containment collar 32 through the various twists and turns of a patient's circulatory or other system.

In FIG. 1B; wire frame 8 is contained in a collapsed state or structure within containment collar 32. In contrast, in FIG. 1C, wire frame 8 is illustrated deployed outside of containment collar 32 in an expanded or deployed state or structure.

Preferably, wire frame 8 is connected to guide wire 4 via a junction 10. This connection may be made by any means, such as soldering, brazing and the like, but may also include wire frame 8 and guide wire 4 being integrally formed together as one unit.

FIGS. 1B–1D show one non-limiting embodiment of wire frame 8 that may be employed in the present invention. Wire frame 8, however, may include any known frame configuration which can be in a collapsed state inside containment collar 32 during insertion into the patient and its travel to or beyond the operative site, which can be transitioned into a deployed state within the patient and which can be returned to a fully or partially collapsed state for removal. Containment collar 32 is not limited to use with wire frame 8, but can be used with any deployable device, that transitions from a collapsed state inside containment collar 32 to a deployed state in a body vessel, canal, organ or open area of any kind in a patient. Preferably, containment collar 32 is generally cylindrical. However, containment collar 32 can have any shape, e.g., square, rectangular, elliptical, trapezoidal, that enables wire frame 8 to transition from a collapsed state to a deployed state.

Where containment collar 32 is used with wire frame 8 having sack 12 thereon, preferably, wire frame 8 must be able to urge a mouth 14 of sack 12 against an inside wall of the body canal or vessel in which sack 12 is positioned in its deployed state so that objects do not pass between mouth 14 of sack 12 and the wall of the patient's body canal or vessel. Mouth 14 of sack 12 is connected to wire frame 8, such as, for example, by gluing or melting mouth 14 of sack 12 to wire frame 8.

In the embodiment shown in FIG. 1C, sack 12 has its mouth 14 connected to an end of wire frame 8, and sack 12 has a closed end or bottom 16 opposite mouth 14. Sack 12 has a generally bag-like shape, preferably a conical shape when deployed. However, sack 12 can have any shape capable of ensnaring objects in the vessel or canal of a patient, e.g., a hemispherical shape.

Guide wire 4 projects through mouth 14 and bottom 16 of sack 12 and terminates at a distal end a distance 18 from bottom 16 of sack 12. Preferably, guide wire 4 extends through and is connected to an apex 20 of bottom 16.

Containment collar 32 has a short generally tubular shape with a lumen 36 of sufficient diameter to enable guide wire 4 to pass therethrough and to contain wire frame 8 and sack 12 in closed configuration within lumen 36 of containment collar 32. The length of containment collar 32 is preferably no greater than needed to contain wire frame 8 and sack 12 therein in a collapsed state during insertion of endovascular device 2 into the patient. Rather, as shown in FIG. 5, containment collar 32 may be shorter still to leave apex 20 exposed when wire frame 8 and sack 12 are in their closed configuration.

A pull wire 34 extends from containment collar 32 to a point external of the patient via the access opening 41 after placement of endovascular device 2 at or beyond the operative site. Pull wire 34 enables containment collar 32 to be pulled proximally, i.e., in the direction illustrated by an arrow 9 in FIG. 1A, while guide wire 4 remains stationary or conversely to advance guide wire 4 distally, i.e., in the direction of an arrow 3, while holding pull wire 34 stationary, whereupon containment collar 32 is pulled off of wire frame 8 or, conversely, wire frame 8 is ejected from containment collar 32 thereby deploying wire frame 8 to its deployed state shown in FIG. 1C. The precise length of pull wire 34 is not limited, as illustrated by the break lines 7, provided pull wire 34 extends from containment collar 32 to a point external of the patient.

With reference to FIGS. 4 and 5, and with continuing reference to FIGS. 1A–1D, pull wire 34 may be attached by any known means, such as gluing, brazing, welding, soldering, integral forming and the like. Preferably, however, containment collar 32 has a portion or area 33 of reduced internal and external diameter. Portion 33 defines a lumen 37 that is continuous with lumen 36 of containment collar 32. Lumens 36 and 37 are of sufficient size to enable guide wire 4 to slide therethrough. Preferably, containment collar 32 is made of a material that shrinks upon application of heat, and portion 33 is formed by applying heat thereto and allowing it to shrink to the extent desired to form portion 33 of reduced diameter. Such heat shrinkable materials are presently available for a wide variety of applications both within and not within the medical arts.

A tubular component 39 is inserted into portion 33 of containment collar 32 prior to the application of heat to portion 33 described above. Heat is then applied to portion 33 thereby causing portion 33 to shrink about the exterior circumference of tubular component 39. In this manner, tubular component 39 frictionally engages containment collar 32, particularly portion 33.

Tubular component 39 is associated with pull wire 34, and tubular component 39 operates to connect pull wire 34 to containment collar 32 via tubular component 39. Pull wire 34 may be connected to tubular component 39 by any various means including, but not limited to, welding, brazing, soldering or integral forming. Preferably, however, tubular component 39 is formed by coiling pull wire 34 adjacent its distal end, as shown in FIG. 4. In this embodiment, tubular component 39 has a lumen 40 which is continuous with lumen 36 of containment collar 32 and is of sufficient diameter to permit guide wire 4 to be slidably received in lumen 40 to permit relative movement between guide wire 4 and containment collar 32 and tubular component 39. The axial length of portion 33 needs only be sufficient to permit tubular component 39 to be sufficiently grasped by containment collar 32 upon application of heat to portion 33 so as to enable endovascular device 2 to be delivered into and removed from a patient without tubular component 39 separating from containment collar 32, but it may be longer.

A length of approximately 12 centimeters for portion 33 ensures that tubular component 39 remains within and does not exit a distal end of a lumen of a guide catheter 42 (shown in FIG. 1a) common to endovascular procedures when wire frame 8 and sack 12 are properly positioned past the lesion. In other words, when wire frame 8 and sack 12 are positioned past a lesion, a length of at least 12 centimeters of portion 33 ensures that tubular component 39 is sufficiently spaced from wire frame 8 and sack 12 that tubular component 39 will remain within the confines of guide catheter 42, as shown in FIG. 1A. Keeping tubular component 39 within the confines of guide catheter 42 is desirable, as it is one less item that can contact the vessel walls and operate to undesirably dislodge particles, e.g., emboli. It is to be appreciated, however, that it is not necessary to use endovascular device 2 with guide catheter 42, and that endovascular device 2 can be positioned in a body canal and/or vessel of a patient without utilizing guide catheter 42.

Containment collar 32 is an important element of the present invention. Unlike known continuous sheaths which, without interruption, extend from a point external of the patient through an access opening 41 and all the way to the operative site to contain an object capture device therein, containment collar 32 of the present invention does not, and is only of such length as is necessary to contain wire frame 8 and sack 12 in a collapsed state. Importantly, containment collar 32 of the present invention does not present a significant anti-torque load along the entire length of guide wire 4 from its distal end at the operative site to its point of access from the body, as do presently available continuous sheaths. Therefore, unlike known sheaths, containment collar 32 does not reduce the torquability of endovascular device 2 of the present invention as will occur with a continuous sheath which extends from the distal end of guide wire 4 at the operative site to access opening 41. This is particularly advantageous during insertion and positioning of endovascular device 2 in a patient.

As noted above, pull wire 34 is of sufficient length to extend from a procedural or surgical site in a vessel to and through access opening 41. For most applications, the length of pull wire 34 is typically at least 100 centimeters long, although any length may be employed as indicated by break lines 7 in FIGS. 1A–1C. Optionally, pull wire 34 may have a handle 38 positioned so as not to interfere with the vascular access site and to aid the surgeon's grasp of pull wire 34. Handle 38 may be permanently or removably affixed to pull wire 34. Alternatively, a pin vice, clamp or similar device that would grasp pull wire 34 and aid the surgeon's grasp of pull wire 34 can be employed.

It is standard clinical practice to position guide wire 4 within guide catheter 42 to direct other surgical instruments into the body along guide wire 4 but within guide catheter 42. More specifically, pliable tip 22; containment collar 32 with wire frame 8 and at least part of sack 12 received therein; tubular component 39 with portion 33 heat shrunk to tubular component 39; the section of guide wire 4 received in tubular component 39 and containment collar 32; the portions of guide wire 4 to either end of containment collar 32; and the portion of pull wire 34 connected to tubular component 39 are inserted into a patient via access opening 41.

Containment collar 32 is guided through the patient's body canal(s) and/or vessel(s) using pliable tip 22 in order to position containment collar 32 to a desired position at and/or adjacent, typically beyond, the operative site. The high degree of torquability resulting from the use of containment collar 32 over any previously available device ensures that the surgeon maintains excellent control over the threading and guiding of endovascular device 2 through the twists and turns of the patient's body canals and/or vessels that are present between access opening 41 and the operative site.

When located at the desired position, pull wire 34 is then pulled proximally in the direction of an arrow 11, illustrated in FIG. 1A, while guide wire 4 is held or otherwise maintained in a stationary position. As pull wire 34 moves in the direction of arrow 11, containment collar 32 moves axial along guide wire 4 relative to sack 12 and wire frame 8, whereupon containment collar 32 is retracted or withdrawn from wire frame 8 and sack 12. This allows wire frame 8 to expand to its deployed state, illustrated in FIG. 1C, whereupon wire frame 8 urges mouth 14 of sack 12 against the blood or other vessel wall, where sack 12 can capture objects dislodged at or near the operative site during the operation. Containment collar 32 may be retracted over guide wire 4, completely removed from the patient's body and withdrawn from guide wire 4 after deployment.

During a procedure, such as, for example, angioplasty or stenting, other over-the-wire or monorail devices may be introduced over guide wire 4. In its deployed state, sack 12 captures the particles dislodged during the procedure.

When the procedure is complete, a tubular retrieval catheter or recovery sheath 6 is advanced over guide wire 4 into the patient, as shown in FIG. 1D. The length of recovery sheath 6 is not limiting to the invention as illustrated by the break lines 52, but recovery sheath 6 must extend from outside the patient's body, where it may be manually manipulated to where sack 12 and wire frame 8 are positioned at the desired position during the procedure. Advancement of recovery sheath 6 in the direction of the arrow 56 causes recovery sheath 6 to advance distally along guide wire 4 over wire frame 8 and, more particularly, each half frame 24 making up wire frame 8 as explained in more detail below, closing mouth 14 of sack 12, and capturing particles 58 received within sack 12. Sack 12 can be retracted partially or completely into recovery sheath 6 and the assembly comprising recovery sheath 6, the captured wire frame 8, and sack 12 are withdrawn from the patient, along with particles 58 captured in sack 12.

In one embodiment of the invention, a prior art support guide wire may be threaded to a location proximal to the desired location; guide catheter 42 introduced over the support guide wire, the support guide wire removed; and endovascular device 2 of the present invention may then be advanced to the desired location through guide catheter 42, where its wire frame 8 and sack 12 are deployed distally of guide catheter 42 and used to capture objects, particles, etc., in the manner described above.

Containment collar 32 is preferably made from Teflon tubing, preferably having a wall thickness less than 0.004 inches, however, containment collar 32 can be made from other flexible biocompatible materials, such as polyethylene, nylon or polyimides, that permit relative axial movement between guide wire 4 and containment collar 32. To promote relative axial movement therebetween when containment collar 32 is made of a material other than Teflon, the inside surface of containment collar 32 and/or guide wire 4 can be coated with a tough flexible lubricious coating, such as Teflon or a hydrophilic film. Moreover, the inside surface of containment collar 32 and/or guide wire 4 can receive a biocompatible lubricant, such as silicon.

With reference to FIG. 2, and with continuing reference to FIGS. 1A–1D, in one embodiment of the present invention, wire frame 8 includes a pair of half frames 24 connected in mirror image relation to guide wire 4 via junction 10. Each half frame 24 has a pair of control arms 26 connected at their proximal ends to guide wire 4 via junction 10. Alternatively, control arms 26 may be integrally formed with the respective half frame 24.

Junction 10 can include any known means of joinder, such as a crimp of biocompatible material; a solder joint of appropriate biocompatible material; or a weld that connects half frames 24 to guide wire 4. The distal end of each half frame 24 has a partial loop 28 that extends between control arms 26. Half frames 24 are preferably fully or partially constructed of a shape-memory-effect alloy, such as Nitinol, in its super-elastic state, although the present invention is not limited to half frames 24 comprised of Nitinol. The shape-memory-effect alloy enables each half frame 24 to be "trained" or formed so that in a relaxed undeformed state control arms 26 diverge between junction 10 and partial loop 28, and partial loop 28 extends transverse, preferably perpendicular, to the longitudinal axis of guide wire 4, with an inside radius of partial loop 28 facing guide wire 4 as illustrated in FIG. 2. Wire frame 8 and, more particularly, half frames 24 and control arms 26 are preferably formed from solid Nitinol, tubular Nitinol or stranded Nitinol.

In another embodiment (not shown), each half frame 24 includes an arcuate section connected to the distal end of each control arm 26. The arcuate sections extend from their respective control arms 26 and terminate with their ends touching or in spaced relation forming a gap therebetween. The arcuate sections can be formed by separating, as for example, by cutting, each partial loop 28 intermediate control arms 26. The arcuate sections can be configured to form a partial or complete loop. In yet another embodiment, wire frame 8 can include a complete loop (not shown) connected to the distal ends of control arms 26. Again, the precise design of wire frame 8 is not limiting to the present invention and any frame design may be employed. Other frame designs, for example, are described in U.S. Pat. Nos. 5,779,716; 5,910,154; 5,911,734; and 6,027,520 which are incorporated herein by reference.

To enable wire frame 8 to be viewed more clearly under fluoroscopic visualization inside a body canal or vessel, a wire or thread 30 made from a biocompatible radiopaque material(s) is wrapped around or bonded to one or more partial loops 28, one or more control arms 26 and/or woven into the rim of mouth 14 of sack 12. For example, stranded Nitinol with a central strand of radiopaque material or Nitinol tubing filled with radiopaque material can be used to form partial loops 28 and/or control arms 26 that can be viewed more clearly under fluoroscopic visualization. Alternatively, partial loops 28 and/or control arms 26 are coated with the biocompatible radiopaque material(s) or a coil of radiopaque material can be wound around each partial loop 28 and/or each control arm 26. To enable pliable tip 22 to be viewed under fluoroscopic visualization inside a body canal or vessel, at least the distal end of pliable tip 22 may be made from or coated with the biocompatible radiopaque material (s). Examples of biocompatible radiopaque material(s) include gold, tungsten and platinum or combinations thereof.

During insertion of deployed wire frame 8 into containment collar 32 during manufacture and/or prior to insertion into a patient, pulling guide wire 4 proximally relative to containment collar 32 causes control arms 26 and partial loops 28 to interact with the inside diameter and distal end of containment collar 32 whereby control arms 26 and partial loops 28 deform and, more particularly, converge toward guide wire 4 as they are received in containment collar 32. As shown in FIG. 3, without containment collar 32 for illustrative purposes, and in FIG. 4, with containment collar 32 present, and in FIG. 5, with both containment collar 32 and sack 12 present, when control arms 26 and partial loops 28 of half frames 24 are received in containment collar 32, they are stressed within the elastic limits of the shape-memory-effect alloy to form elongated loops having axes positioned substantially parallel to the longitudinal axis of guide wire 4. The super-elastic property of the shape-memory-effect alloy enables half frames 24 to return to the relaxed undeformed shape, shown in FIG. 2, when they are deployed from containment collar 32 in the manner described above.

Sack 12 is formed of a biocompatible material having sufficient strength to withstand forces associated with deployment in body canals or vessels and forces associated with ensnaring/retaining particles, objects, etc., within sack 12. The material may be either non-porous or porous, but is preferably porous. Sack 12 made of non-porous material occludes flow in the vessels. Sack 12 made of porous material allows flow of a fluid, e.g., blood, in the vessels, and permits particles of smaller diameter than the pores of sack 12 to escape therethrough. Preferably, sack 12 is formed from a polymeric material, such as polyurethane, which is either porous or non-porous. Sack 12 can also be made radiopaque through the addition thereto of barium sulfate or bismuth sulfate or threads of radiopaque materials interwoven or otherwise associated with sack 12. Sack 12 can also be made of other biocompatible materials, such as woven polyester fabrics.

A rim of mouth 14 of sack 12 surrounds and is bonded to half frames 24 to secure sack 12 to wire frame 8. Similarly, apex 20 of bottom 16 of sack 12 is bonded to the projection of guide wire 4 therethrough to secure sack 12 to guide wire 4. Chemicals and/or heat can be utilized to bond sack 12 to guide wire 4 and wire frame 8. Preferably, sack 12 is bonded between half frames 24 and guide wire 4 so that no gaps exist between sack 12 and guide wire 4, and sack 12 and wire frame 8.

Sack 12 preferably has a conical shape as illustrated in FIG. 1C. However, sacks having more hemispherical shapes, as illustrated in FIGS. 2, 6, 9, 10 and 11 of U.S. Pat. No. 5,779,716 may also be employed. Conical-shaped sacks have the advantage that as objects, particles, etc. fill bottom 16 of sack 12, sack 12 still permits flow of fluid, e.g., blood, into and out of sack 12 proximal of the build up of particles, objects, etc. in sack 12, as illustrated in FIG. 6.

The size of the body canal and/or vessel, more particularly, the diameter of the lumen of the vessel in which endovascular device 2 of the present invention is to be deployed, establishes the dimensions of mouth 14 of sack 12 when wire frame 8 is in its deployed state that can be utilized to capture particles, objects, etc. Specifically, the dimensions of wire frame 8 in its deployed state are selected so that mouth 14 of sack 12 is urged snugly with the intima of the vessel. Preferably, wire frame 8 is configured to be firm and pliable so that interaction between wire frame 8 and the intima of the vessel avoids trauma to the vessel and yet provides a firm or snug opposition between mouth 14 of sack 12 and the intima of the vessel. In an exemplary embodiment, control arms 26 and partial loops 28 of wire frame 8 have diameters between 0.003 to 0.010 inches (0.0076 cm to 0.025 cm), guide wire 4 has a diameter between 0.010 to 0.035 inches (0.025 cm to 0.088 cm), and containment collar 32 has an outside diameter between 0.025 to 0.130 inches (0.064 cm to 0.33 cm).

The lengths of pull wire 34 and guide wire 4 are selected based on the position of access opening 41 for inserting endovascular device 2 in the lumen of the body canal and/or vessel relative to the position in the lumen of the solid material capable of producing movement of particles, as described above.

Endovascular device 2 can be used in several ways depending on its exact configuration and the area of the cardiovascular system involved. By way of a specific non-limiting but illustrative example, interventional use of endovascular device 2 to capture emboli shed during a procedure, such as angioplasty and stent placement, to treat a stenosis in the carotid artery of a human patient, will now be described with reference to FIGS. 1A–1D, 5 and 6.

Starting with wire frame 8 and sack 12 received in containment collar 32 and with at least pliable tip 22 extending from containment collar 32, endovascular device 2 is inserted percutaneously into the patient through guide catheter 42 previously inserted in access opening 41 in the patient's femoral artery. Under fluoroscopic visualization, guide wire 4 is manipulated to advance pliable tip 22 and containment collar 32 through guide catheter 42 in the patient's circulatory system until reaching the carotid artery. Guide wire 4 is further advanced beyond guide catheter 42, guided by pliable tip 22 through the remainder of the carotid artery to, across and beyond a stenosis in the internal carotid artery. Containment collar 32 is now positioned at a desired position in the internal carotid artery so that, when deployed, wire frame 8 and sack 12 are downstream of the stenosis in the internal carotid artery to capture and retain any dislodged emboli particles.

To deploy wire frame 8 and sack 12, a portion of guide wire 4 outside the patient's body is held steady and a portion of pull wire 34, or handle 38, outside the patient's body is grasped and pulled in the direction of arrow 11 so that containment collar 32 is retracted or withdrawn from over wire frame 8 and sack 12, thereby enabling wire frame 8 to deploy and to hold mouth 14 of sack 12 snugly against the wall of the internal carotid artery.

Thereafter, containment collar 32 is pulled in the direction of arrow 11 while guide wire 4 remains stationary until containment collar 32 is removed completely from guide wire 4 and the patient, thereby enabling other over-the-wire or monorail devices or components used during the procedure to be received on guide wire 4 and delivered through guide catheter 42 to the stenosis. Other over-the-wire or monorail devices include, but are not limited to, endovascular devices such as dilation balloon systems, stent deployment systems, mechanical and/or laser thrombectomy devices and combinations thereof that track over guide wire 4 and are used to reduce the stenosis.

With regard to stent deployment systems, the stent may be either a self-expanding stent or a mechanically expandable stent. Stents are usually in the form of a tubular mesh sleeve. See, for example, U.S. Pat. No. 4,733,665 to Palmaz, incorporated herein by reference. Either type of stent is typically delivered via a stent catheter.

For the mechanically expandable stent, the stent catheter includes at or near its distal end an inflatable balloon on which the stent is mounted. An inflation lumen runs the length of the stent catheter to the balloon. The stent catheter includes a guide lumen which runs the length of the stent catheter and which is configured to receive guide wire 4 therein. In use, the proximal end of guide wire 4 is inserted into the guide lumen of the stent catheter. Thereafter, the stent catheter is advanced on guide wire 4 until the inflatable balloon on which the stent is mounted is positioned at an appropriate point in the vessel, e.g., wholly or partially across a stenosis. Thereafter, the balloon is expanded via the inflation lumen causing the stent, in turn, to expand and in its expanded state to hold itself with a frictional fit against the walls of the vessel into which it has been inserted.

The self-expanding stent is typically made in whole or part from a shape-memory-effect alloy and is compressed within a delivery catheter until deployment. Pushing the stent from the delivery catheter deploys the stent to an expanded state, much in the same manner as wire frame 8 expands upon release from containment collar 32.

An unfortunate aspect of stents that are of the tubular mesh design is that they tend to create particles, e.g., emboli, due to their open mesh structure. As they expand, embolic material is able to disperse through the mesh to the interior of the stent where the flow of blood or other fluid undesirably washes particles of embolic material downstream in the circulatory or other system. Further, even after successful implantation, the open mesh structure tends to permit stenotic material to build up through the mesh that could again occlude the artery. Therefore, in a preferred embodiment of the present invention, where the system includes endovascular device 2 of the present invention, and where additional over-the-wire stent deployment systems are used as part of the system, the stent preferably includes a sheathing or coating material associated with the open mesh structure of the stent. This material may be on the outside of the stent, the inside lumen of the stent, or both. The stent may also be embedded within an envelope of such material. Such material is biocompatible and operates to prevent stenotic material from advancing from the walls of the vessel through the open mesh structure of the stent and into the circulatory or other system during implantation of the stent. Examples of suitable materials for encasing all or a portion of the stent include, but are not limited to, Dacron, Gortex and combinations thereof.

After the stenosis has been reduced and the other over-the-wire or monorail components are removed from guide wire 4, recovery sheath 6 is positioned over guide wire 4 and advanced through guide catheter 42, if guide catheter 42 has been permitted to remain in the patient up to this point toward, and beyond the operative site to contact wire frame 8 and sack 12. As the lumen of the carotid artery in this region has now been expanded, in this example, by the stent, recovery sheath 6 may safely have a larger diameter than containment collar 32 without the danger of dislodging stenotic material. Further, recovery sheath 6 may be more easily advanced through the operative site now that the lumen has been expanded. Further advancement of recovery sheath 6 in the direction of arrow 56 and/or pulling of guide wire 4 in the direction of arrow 11, causes all or a portion of wire frame 8 and all or a portion of sack 12 to be retracted into recovery sheath 6 to a desired extent.

As shown in FIG. 6, particles 58 captured in sack 12 may permit only partial retraction of sack 12 into recovery sheath 6. Preferably, however, particles 58 captured in sack 12 cannot empty or escape into the artery. Thereafter, recovery sheath 6, wire frame 8 and sack 12, with particles 58 captured in sack 12, are withdrawn from the patient along with guide wire 4.

Figure 7A:
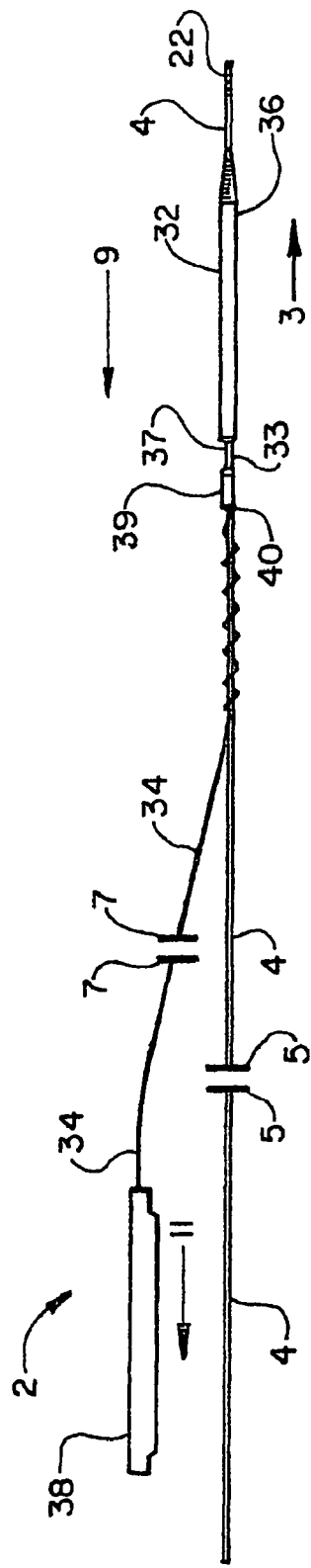
FIG. 7A is a side view showing coiling of a pull wire around the guide wire.
Figure 7B:
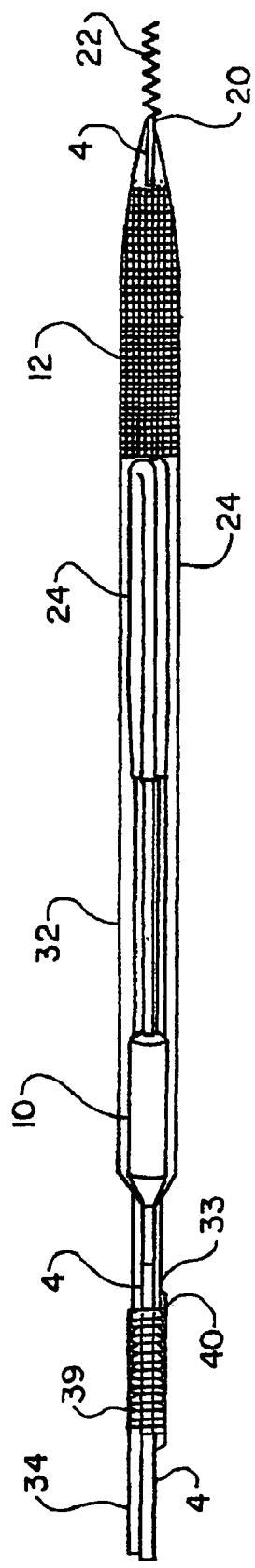
FIG. 7B is a partial cross-sectional side view of the present invention showing an alternate embodiment for affixing the pull wire to the containment collar.

Referring now to FIGS. 7A and 7B, there is illustrated an alternative embodiment of the present invention, illustrating tubular component 39 attached to the external surface of portion 33 of containment collar 32, and further illustrating pull wire 34 coiled about guide wire 4 to contain its lateral movement in the patient. The degree of coiling is preferably within the range of coiling that retains pull wire 34 closely adjacent guide wire 4, but not so great as to undesirably reduce torquability of the device. In this embodiment, containment collar 32 has the same portion 33, and lumen 36 of containment collar 32 remains continuous with lumen 37 of portion 33 to permit containment collar 32 to be slidably advanced over guide wire 4. However, in this embodiment, portion 33 is firmly gripped about its exterior by tubular component 39 as illustrated in FIGS. 7A and 7B, which tubular component 39 is in turn associated with pull wire 34 to connect pull wire 34 to containment collar 32 through tubular component 39. Again, pull wire 34 may be connected to tubular component 39 by any of various means including, but not limited to, welding, brazing, soldering or integral forming, as for example, where tubular component 39 is formed by coiling pull wire 34 as described above. In this embodiment, lumen 40 of tubular component 39 is of sufficient diameter to accept the external diameter of portion 33 in a preferably frictional fit of sufficient grasp so as to enable endovascular device 2 to be delivered into and removed from a patient without tubular component 39 separating from containment collar 32.

The axial length of portion 33 need only be sufficient to permit tubular component 39 to grasp containment collar 32 sufficiently firmly so as to enable endovascular device 2 to be delivered into and removed from a patient without tubular component 39 separating from containment collar 32, but it may be longer. A length of approximately 12 centimeters of the length of portion 33 ensures that tubular component 39 remains within and does not exit the distal end of the lumen of guide catheter 42 common to most all endovascular procedures when wire frame 8 and sack 12 are properly positioned past the lesion. In other words, when wire frame 8 and sack 12 are positioned past a lesion, a length of at least 12 centimeters for portion 33 ensures that tubular component 39 is sufficiently distanced from wire frame 8 and sack 12 that tubular component 39 will remain within the confines of guide catheter 42. Keeping tubular component 39 within the confines of guide catheter 42 is desirable, as it is one less item that can contact the vessel walls and undesirably dislodge particles.

Figure 8:
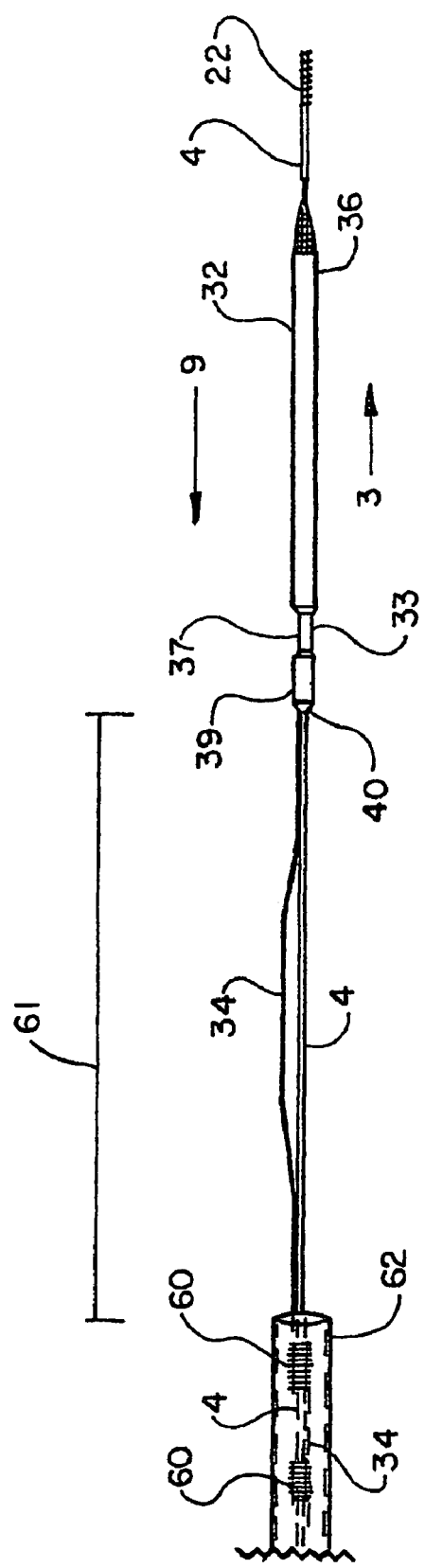
FIG. 8 is a perspective view of another embodiment of the present invention for affixing the pull wire about the guide wire and further illustrating the use of a guide catheter.

Referring now to FIG. 8, there is illustrated yet another embodiment of the present invention wherein pull wire 34 includes one or more coiled sections 60, illustrated in phantom. Each coiled section 60 is preferably displaced at least a distance 61 proximally of tubular component 39 such that when endovascular device 2 is deployed in a body canal or vessel, coiled section 60 remains within the confines of a guide catheter 62. In this embodiment, the torquability of endovascular device 2 is not compromised. Also, this embodiment ensures that no coiling will be present in distance 61 between guide catheter 62 and the procedure site, which is preferred as such coiling could irritate vessel walls or undesirably dislodge particles. Although two coiled sections 60 are illustrated in FIG. 8, additional coiled sections 60 may be positioned along the length of guide wire 4.

Figure 9A:
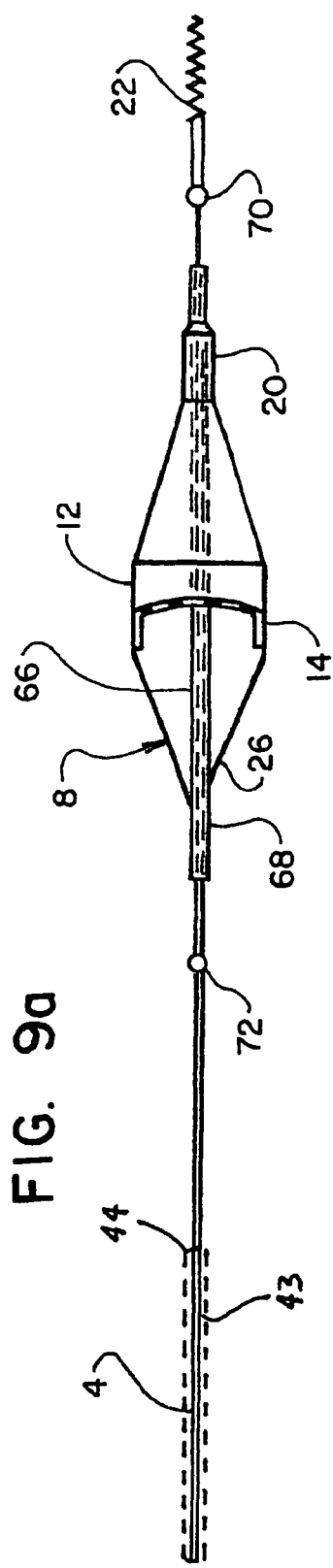
FIGS. 9A and 9B are different side views of another embodiment of the present invention showing a wire frame and filter slidably received on the guide wire.
Figure 9B:
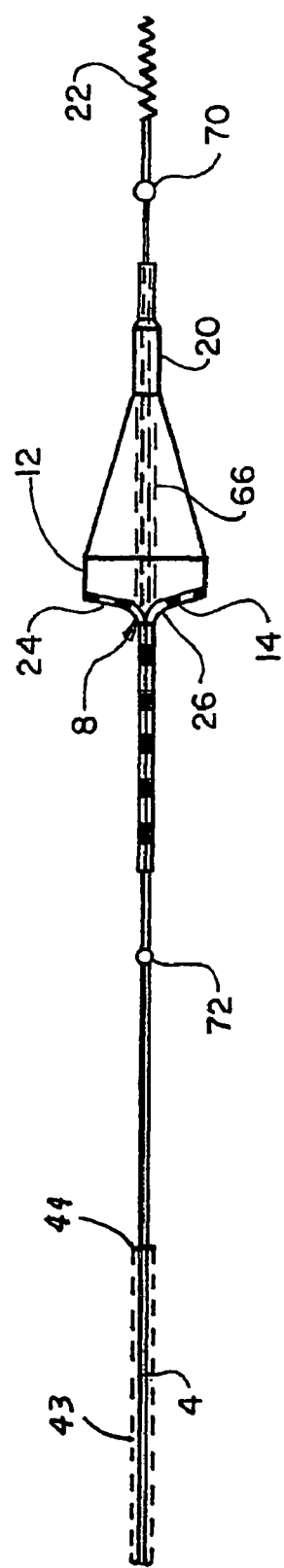

Referring now to FIGS. 9A and 9B, a side view and a rotated side view, respectively, of an object capture device in accordance with another embodiment of the present invention are illustrated. In this embodiment, wire frame 8 and sack 12 are connected to a tightly wound but flexible coil of wire 66, or spring, which defines a lumen 67 therethrough. Preferably, coil of wire 66 is helically wound in the form of a cylinder. The proximal end of control arms 26 are connected to coil of wire 66 at a junction 68 adjacent one end of coil of wire 66, and apex 20 of sack 12 is connected to coil of wire 66 adjacent the other end of coil of wire 66. The proximal ends of control arms 26 can be connected to coil of wire 66 via junction 68 in the same manner as control arms 26 are connected to guide wire 4 via junction 10 in FIG. 2. Coil of wire 66 is configured to be firm axially, but pliable laterally. This enables coil of wire 66 to bend and follow the path of guide wire 4 in a body canal or vessel while avoiding axial elongation of coil of wire 66 which may cause tension to be applied to wire frame 8 and/or sack 12 between junction 68 and apex 20 of sack 12. A distal stop 70 and a proximal stop 72 are connected in spaced relation to guide wire 4. Stops 70 and 72 are each formed from a solder joint of biocompatible material or a weld.

In use, guide wire 4 is received in lumen 67 and coil of wire 66 is received on guide wire 4 between stops 70 and 72 which prevent coil of wire 66, and hence, wire frame 8 and sack 12, from moving on guide wire 4 distally of distal stop 70 and proximally of proximal stop 72. More specifically, stops 70 and 72 have a diameter larger than the inside diameter of coil of wire 66 thereby preventing slidable movement of coil of wire 66 axially along guide wire 4, distally of distal stop 70 or proximally of proximal stop 72.

Starting with wire frame 8 and sack 12 received in containment collar 32 and with coil of wire 66 received on guide wire 4 between stops 70 and 72, pliable tip 22 is inserted percutaneously into the patient through the proximal end of guide catheter 42 previously inserted in access opening 41. Guide wire 4 is manipulated to advance pliable tip 22, coil of wire 66, containment collar 32 and pull wire 34 through guide catheter 42 until pliable tip 22 approaches the distal end of guide catheter 42. Next, guide wire 4 is further advanced beyond the distal end of guide catheter 42, guided by pliable tip 22, until containment collar 32 is positioned at a desired position in a body canal or vessel. Because coil of wire 66 is flexible laterally, it is able to conform to twists and bends taken by guide wire 4 during manipulation to advance containment collar 32 to the desired position.

Once containment collar 32 is at the desired position, a portion of pull wire 34, or handle 38, outside the patient's body is pulled proximally while, at the same time, a portion of guide wire 4 outside the patient's body is held stationary. Pulling pull wire 34 or handle 38 proximally causes containment collar 32 to be retracted or withdrawn from over wire frame 8 and sack 12 whereupon wire frame 8 deploys and holds mouth 14 of sack 12 snugly against the wall of a body canal or vessel. Thereafter, pull wire 34 and containment collar 32 are pulled proximally through guide catheter 42 while guide wire 4 remains stationary until containment collar 32 is completely removed from guide wire 4.

Alternatively, containment collar 32 is omitted and replaced by a deployment catheter 43 (shown in phantom in FIGS. 9A and 9B) which has a lumen 44 of sufficient inside diameter to receive guide wire 4 and coil of wire 66, with wire frame 8 and sack 12 in their collapsed state, therein. Starting with coil of wire 66 received on guide wire 4 between stops 70 and 72, with wire frame 8 and sack 12 received in their collapsed state in lumen 44 adjacent the distal end of deployment catheter 43 received on guide wire 4, and with pliable tip 22 extending from the distal end of the deployment catheter 43, pliable tip 22 and the distal end of deployment catheter 43 are inserted percutaneously into the patient through guide catheter 42 previously inserted in access opening 41. Deployment catheter 43 and guide wire 4 are manipulated so that the distal end of deployment catheter 43 and pliable tip 22 advance through guide catheter 42 until pliable tip 22 approaches the distal end of guide catheter 42. Next, the distal end of deployment catheter 43 and guide wire 4 are further advanced beyond guide catheter 42, guided by pliable tip 22, until coil of wire 66 is positioned at a desired position in a body canal or vessel.

Once coil of wire 66 is at the desired position, a portion of deployment catheter 43 outside the patient's body is pulled proximally while, at the same time, a portion of guide wire 4 outside the patient's body is held stationary. Pulling deployment catheter 43 in this manner causes deployment catheter 43 to be retracted or withdrawn from over wire frame 8 and sack 12 whereupon wire frame 8 deploys and holds mouth 14 of sack 12 snugly against the wall of a body canal or vessel. Thereafter, deployment catheter 43 is pulled proximally through guide catheter 42, while guide wire 4 remains stationary, until deployment catheter 43 is completely removed from guide wire 4.

Next, an over-the-wire or monorail device or component can be received on guide wire 4 and delivered through guide catheter 42 to a position proximal of proximal stop 72 to perform a procedure that the particular over-the-wire or monorail device is configured to perform. Once the procedure has been performed, the over-the-wire or monorail device is withdrawn from guide wire 4 through guide catheter 42.

Thereafter, recovery sheath 6, of the type shown in FIG. 1D, is positioned over guide wire 4 and is advanced distally thereon through guide catheter 42 to contact wire frame 8. Further advancement of recovery sheath 6 distally on guide wire 4 causes all or a portion of wire frame 8 and all or a portion of sack 12 to be retracted into recovery sheath 6 to a desired extent. Thereafter, recovery sheath 6, wire frame 8 and sack 12 with any particles 58 captured in sack 12 are withdrawn from the patient along with guide wire 4.

Guide wire 4 and lumen 67 and are configured to enable rotation of guide wire 4 in coil of wire 66. Distal and proximal stops 70 and 72 are spaced so that coil of wire 66 can reside between them. If the spacing between distal and proximal stops 70 and 72 is slightly greater than the length of the coil of wire 66, guide wire 4 can only rotate in lumen 67. Such ability to rotate is important to prevent loading of the guide wire 4 to reduce its torquability. If spacing between distal and proximal stops 70 and 72 is greater than the length of coil of wire 66, coil of wire 66 can rotate in lumen 67 and can move linearly along the guide wire 4. Thus, when deployed, wire frame 8 does not rub the wall of the body canal or vessel in response to longitudinal movement of guide wire 4 that does not move distal stop 70 or proximal stop 72 into contact with coil of wire 66.

With continuing reference to FIGS. 9a and 9b, in another embodiment, proximal stop 72 is omitted, wire frame 8 and sack 12 are connected to coil of wire 66, wire frame 8 and sack 12 are received in containment collar 32, guide wire 4 is received in lumen 67, and coil of wire 66 is received on guide wire 4 between distal stop 70 and the distal end of deployment catheter 43 received on guide wire 4 proximally of distal stop 70. Lumen 44 has a sufficient inside diameter to slidably receive guide wire 4 therein. However, in this embodiment, lumen 44 is sufficiently small whereupon the distal end of deployment catheter 43 abuts an end of coil of wire 66 when deployment catheter 43 and coil of wire 66 are received on guide wire 4.

In use, pliable tip 22 and containment collar 32, with the distal end of deployment catheter 43 abutting the proximal end of coil of wire 66 having guide wire 4 received in lumen 67, are inserted percutaneously into the patient through a lumen of guide catheter 42 which has been previously inserted in access opening 41. Guide wire 4 and deployment catheter 43 are manipulated to advance pliable tip 22, containment collar 32 and coil of wire 66 through guide catheter 42 until pliable tip 22 approaches the distal end of guide catheter 42. More specifically, guide wire 4 and deployment catheter 43 are urged distally while, at the same time, a portion of guide catheter 42 outside of the patient's body is held stationary whereupon pliable tip 22, containment collar 32, coil of wire 66, deployment catheter 43 and guide wire 4 advance through guide catheter 42. In this embodiment, pull wire 34 extends through the lumen of guide catheter 42 and, more particularly, pull wire 34 is disposed between the interior surface of guide catheter 42 and the exterior surface of deployment catheter 43. Next, pliable tip 22 and containment collar 32 are urged beyond the distal end of guide catheter 42, guided by pliable tip 22, until coil of wire 66 and containment collar 32 are positioned at a desired position in a body canal or vessel.

Alternatively, pliable tip 22 of guide wire 4 is first inserted percutaneously into the patient through a lumen of guide catheter 42 which has been previously inserted in access opening 41. Guide wire 4 is manipulated to advance pliable tip 22 to the distal end of the guide catheter 42. Pliable tip 22 is urged beyond the distal end of guide catheter 42 until distal stop 70 is positioned at a desired position in the body canal or vessel. Thereafter, deployment catheter 43 and coil of wire 66, with wire frame 8 and sack 12 received in containment collar 32, are received on guide wire 4 with the proximal end of containment collar 32 enclosing the distal end of deployment catheter 43 as it abuts the proximal end of coil of wire 66. Next, deployment catheter 43 is manipulated through guide catheter 42 along guide wire 4, while guide wire 4 and guide catheter 42 are held stationary, to advance coil of wire 66 and containment collar 32 over guide wire 4 toward distal stop 70 and to a desired position in the body canal or vessel. Pull wire 34 extends through the lumen of guide catheter 42 and, more particularly, pull wire 34 is disposed between the interior surface of guide catheter 42 and the exterior surface of deployment catheter 43.

Once coil of wire 66 and containment collar 32 are at the desired position in the body canal or vessel, a portion of pull wire 34, or handle 38, outside the patient's body is pulled proximally while, at the same time, portions of guide catheter 42 and deployment catheter 43 outside the patient's body are held stationary. In response to pulling pull wire 34 or handle 38 proximally, tubular component 39 and containment collar 32 advance proximally over deployment catheter 43 whereupon wire frame 8 deploys and holds mouth 14 of sack 12 snugly against the wall of the body canal or vessel. Proximal advancement of tubular component 39 and containment collar 32 over deployment catheter 43 continues until they are received in guide catheter 42. Thereafter, deployment catheter 43, tubular component 39 and containment collar 32 are removed from guide catheter 42 and guide wire 4.

Next, an over-the-wire or monorail device or component can be received on guide wire 4 and delivered through guide catheter 42 to a position proximal of wire frame 8 and sack 12 to perform the procedure the over-the-wire or monorail device or component is configured to perform. Once the procedure has been performed, the over-the-wire or monorail device or component is withdrawn from guide catheter 42 and guide wire 4.

Thereafter, recovery sheath 6 is positioned over guide wire 4 and advanced distally thereon through guide catheter 42 to contact wire frame 8. Further advancement of recovery sheath 6 distally on guide wire 4 causes all or a portion of wire frame 8 and/or all or a portion of sack 12 to be retracted into recovery sheath 6 to a desired extent. Thereafter, recovery sheath 6, wire frame 8 and sack 12, and any particles 58 captured in sack 12, are withdrawn from the patient along with guide wire 4.

Recovery sheath 6 in FIG. 1D is shown as having an elongated tubular form. However, a retrieval catheter assembly 100 of the type shown in FIGS. 10A–10C can be utilized to retrieve wire frame 8 and sack 12. Retrieval catheter assembly 100 includes in coaxial arrangement having an inner tube 102 and an outer tube 104. Inner tube 102 includes a lumen 106 configured to slidably receive guide wire 4 therein, while outer tube 104 includes a lumen 108 configured to slidably receive inner tube 102 therein.

Outer tube 104 is connected at its proximal end to a fitting 110. Fitting 110 has a lumen 111 configured to slidably receive inner tube 102 therethrough. A Y-connector 112 is slidably received on inner tube 102 and guide wire 4 on a side of fitting 110 opposite wire frame 8 and sack 12. A fitting 114 is coupled to an end of inner tube 102 opposite wire frame 8 and sack 12. Fitting 114 includes a lumen 115 configured to slidably receive guide wire 4 therethrough when fitting 114 is connected to inner tube 102. Fittings 110 and 114 are configured to be mated to opposite ends of Y-connector 112. More specifically, fittings 110 and 114 include female threads (not shown) configured to be threadably mated with male threads (not shown) formed on opposite ends of Y-connector 112. In one embodiment, Y-connector 112 includes a male threaded side port 118 having a female threaded cap 116 threadably mated thereon.

Y-connector 112 is configured in a manner known in the art to enable guide wire 4 and inner tube 102 to be received therethrough while avoiding the undesired seepage of fluid from a body canal or vessel via lumen 106 of inner tube 102 when wire frame 8 and sack 12 are deployed in a body canal or vessel of a patient. Cap 116 can be removed from side port 118 so that a syringe can be received in side port 118 for introducing fluids into the body canal or vessel of the patient via lumen 108 of outer tube 104 when inner tube 102 is loosely received therein. Preferably, however, inner tube 102 and outer tube 104 fit snugly and slidably together in a manner that avoids the effective passage of fluid in lumen 108. Similarly, guide wire 4 and inner tube 102 fit snugly and slidably together in a manner that avoids the effective passage of fluid in lumen 106.

At an appropriate time, with fittings 110 and 114 coupled to Y-connector 112, retrieval catheter assembly 100 is positioned over guide wire 4 and advanced distally thereon, preferably through guide catheter 42, to contact wire frame 8. Preferably, during advancement of inner tube 102 on guide wire 4, the distal end of inner tube 102 extends distally out of lumen 108 a short distance as shown in FIG. 10A. Because of the snug and slidable fit between guide wire 4 and inner tube 102 and since the distal end of inner tube 102 extends distally out of lumen 108 when retrieval catheter assembly 100 is slidably advanced on guide wire 4, inner tube 102 and outer tube 104 accurately track the path of guide wire 4 in the body canal or vessel of the patient in a manner that avoids the distal end of inner tube 102 or the distal end of outer tube 104 from contacting a protrusion or a stent deployed in a body canal or vessel of the patient, or from contacting the intima of the body canal or vessel where guide wire 4 makes relatively sharp turns therein.

When the distal end of inner tube 102 is contacting or is closely adjacent the connection of wire frame 8 to guide wire 4, fitting 114 is uncoupled from Y-connector 112. Thereafter, fitting 114 is pulled proximally whereupon inner tube 102 moves proximally on guide wire 4 and is retracted into lumen 108 of outer tube 104, and Y-connector 112 is advanced distally on guide wire 4 whereupon the distal end of outer tube 104 advances over wire frame 8 and, if desired, over sack 12 to a desired extent. Preferably, Y-connector 112 is advanced sufficiently distally that all of wire frame 8 and all or a portion of sack 12 are received in the space in lumen 108 between the distal end of inner tube 102 and the distal end of outer tube 104. Alternatively, with Y-connector 112 held stationary, guide wire 4 can be pulled proximally so that all of wire frame 8 and all or a portion of sack 12 are retracted into lumen 108 in the space between the distal end of inner tube 102 and the distal end of outer tube 104. Thereafter, retrieval catheter assembly 100, and more particularly, inner tube 102 and outer tube 104 with wire frame 8 and sack 12 partially or wholly received in lumen 108, are withdrawn from the patient along with guide wire 4.

Referring now to FIGS. 11A and 11B, a perspective view and a side view, respectively, of another embodiment of a wire frame 134 for use with the object capture device of the present invention is illustrated. In this embodiment, sack 12 is connected to wire frame 134 which includes an arm 136 connected at one end to a junction 138 and at another end to a loop 140 to which mouth 14 of sack 12 is connected. Arm 136 and loop 140 are formed from a shape-memory-effect alloy which can be received in a collapsed state or structure within containment collar 32, recovery sheath 6 or outer tube 104 of retrieval catheter assembly 100 in the same manner as half frames 24 and control arms 26 of wire frame 8. In addition, arm 136 and loop 140 can be deployed outside of containment collar 32 in its expanded or deployed state or structure shown in FIGS. 11A and 11B. Arm 136 extends distally from its connection to junction 138 and radially away from guide wire 4. Guide wire 4 extends through mouth 14, loop 140 and apex 20 of sack 12. Apex 20 and junction 138 can be coupled to guide wire 4. Alternatively, apex 20 and junction 138 can be slidably received on guide wire 4 between a pair of stops, e.g., distal stop 70 and proximal stop 72, of the type shown in FIGS. 9A and 9B.

As can be seen from the foregoing, endovascular device 2 of the present invention provides several important advantages over other systems. These include, but are not limited to, the device's ability to enable emboli shed during angioplasty and stenting procedures to be safely captured and removed. Its design facilitates scaling for use in various diameter vessels. The shape-memory-effect alloy permits wire frame 8 to closely conform with the intima of a blood vessel while avoiding trauma to the blood vessel. Pliable tip 22 and/or the extension of the distal end of guide wire 4 the distance 18 beyond bottom 16 of sack 12 permits manipulation of endovascular device 2 through tortuous vascular configurations, and containment collar 32 permitting such manipulation without the undesirable reduction of torquability associated with presently available systems. Guide wire 4 enables delivery of other devices to the lesion site. Sack 12 connected to wire frame 8 acts to form a basket that can be manipulated to a position outside containment collar 32 where the mouth of the basket is open and a position inside containment collar 32 where the mouth of the basket is closed, and vice versa. The material used to construct sack 12 can be porous or non-porous. When sack 12 is made of a porous material, it acts as a filter that allows blood to flow and captures particles of a size greater than the pores. When sack 12 is made of a non-porous material, it occludes blood flow and movement of solid particles thereby.

In an alternative embodiment, a suction device can be used to remove particles trapped by sack 12 made of non-porous material.

The present invention may be employed to capture objects in body organs, cavities, canals or other structures within the body, so as to facilitate the entrapment within and/or removal of the object from the body. The apparatus of the present invention may be positioned and employed to capture the object using fluoroscopic visualization in general and angiography with dye injection in particular, among other positioning methods and devices. The present invention may be utilized in any medical procedure where it is desirable to entrap particles in blood or other vessels, but is particularly advantageous for use with endovascular procedures including, but not limited to, mechanical and laser thrombectomy, angioplasty and stenting operations to dilate occluded vessels and yet minimize embolic events.

The invention has been described with reference to the preferred embodiments. Obvious modifications and alterations will occur to others upon reading and understanding the preceding detailed description. For example, while endovascular device 2 has been described in connection with containment collar 32 being utilized with wire frame 8 and sack 12, it is to be appreciated that containment collar 32 can be utilized to deploy other configurations of collapsible or resilient frames having a sack, basket or filter attached thereto. Non-limiting examples of the types of collapsible or resilient frames and filters that can be deployed using containment collar 32 include those illustrated in U.S. Pat. No. 6,129,739 to Khosravi; U.S. Pat. No. 6,152,946 to Broome et al.; U.S. Pat. No. 6,179,861 to Khosravi et al.; and International Publication Nos. WO 96/01591 and WO 99/23976, the disclosures of which are incorporated herein by reference. It is intended that the invention be construed as including all such modifications and alterations insofar as they come within the scope of the appended claims or the equivalents thereof.

I claim:

1. An apparatus for removing a solid object from a body canal or vessel, the apparatus comprising:

a wire frame;

a coil of wire having two ends and helically wound in the form of a cylinder defining a lumen therethrough, said coil of wire being capable of rotation or linear movement when positioned on a guide wire, said coil of wire further configured to be firm axially, but pliable laterally, such that said coil of wire can conform to twists and bends taken by said guide wire during manipulation and advancement of said guide wire;

a sack affixed to said wire frame, said sack having an apex, wherein said apex of said sack is connected to one of said ends of said coil of wire;

control arms attached to said wire frame and having proximal ends connected near the other end of said coil of wire via a junction;

whereby said coil of wire can bend and follow a path of said guide wire while avoiding axial elongation of said coil of wire.

2. The apparatus of claim 1, wherein said guide wire includes a proximal stop and a distal stop in spaced relation on said guide wire; said coil of wire is received on said guide wire between said proximal stop and said distal stop; and each said stop is configured to avoid the slidable passage of said coil of wire thereby.

3. The apparatus of claim 1, further comprising a containment collar configured to slidably receive the guide wire therethrough and to receive at least part of the frame therein.

4. The apparatus of claim 3, further comprising a pull wire connected to said containment collar.

* * * * *